US006887214B1

(12) United States Patent
Levin et al.

(10) Patent No.: US 6,887,214 B1
(45) Date of Patent: May 3, 2005

(54) BLOOD PUMP HAVING A DISPOSABLE BLOOD PASSAGE CARTRIDGE WITH INTEGRATED PRESSURE SENSORS

(75) Inventors: Howard R. Levin, Teaneck, NJ (US); Mark Gelfand, New York, NY (US); Steven Bernard, Yonkers, NY (US)

(73) Assignee: CHF Solutions, Inc., New York, NY (US)

( * ) Notice: Subject to any disclaimer, the term of this patent is extended or adjusted under 35 U.S.C. 154(b) by 220 days.

(21) Appl. No.: 09/660,195

(22) Filed: Sep. 12, 2000

(51) Int. Cl.[7] .......................... A61M 37/00; C02F 1/44

(52) U.S. Cl. .................... 604/6.11; 604/6.09; 604/4.01; 210/645

(58) Field of Search .............................. 604/5.01, 6.09, 604/6.11, 65–67; 210/90, 94, 409, 461, 418, 428, 435, 645–647, 252, 258–260; 422/44–48

(56) References Cited

U.S. PATENT DOCUMENTS

| | | | |
|---|---|---|---|
| 4,086,924 A | | 5/1978 | Latham, Jr. |
| 4,229,299 A | * | 10/1980 | Savitz et al. ................ 210/137 |
| 4,436,620 A | * | 3/1984 | Bellotti et al. ........... 210/321.8 |
| 4,599,055 A | | 7/1986 | Dykstra |
| 4,657,529 A | | 4/1987 | Prince et al. |
| 4,679,567 A | | 7/1987 | Hanlon et al. |
| 4,784,768 A | | 11/1988 | Mathieu |
| 4,824,339 A | | 4/1989 | Bainbridge et al. |
| 4,838,865 A | * | 6/1989 | Flank et al. ................ 604/118 |
| 4,936,980 A | | 6/1990 | Yoshimichi et al. |
| 4,960,127 A | | 10/1990 | Noce et al. |
| 5,114,580 A | | 5/1992 | Ahmad et al. |
| 5,312,550 A | | 5/1994 | Hester |
| 5,366,630 A | | 11/1994 | Chevallet |
| 5,392,653 A | | 2/1995 | Zanger et al. |
| 5,410,916 A | * | 5/1995 | Cook ......................... 600/561 |
| 5,536,237 A | | 7/1996 | Prince et al. |
| 5,581,038 A | | 12/1996 | Lampropoulos et al. |
| 5,679,245 A | * | 10/1997 | Manica ....................... 210/134 |
| 5,685,989 A | | 11/1997 | Krivitski et al. |
| 5,707,086 A | | 1/1998 | Treu et al. |
| 5,725,776 A | | 3/1998 | Kenley et al. |
| 5,730,712 A | | 3/1998 | Falkvall et al. |

(Continued)

FOREIGN PATENT DOCUMENTS

| | | |
|---|---|---|
| DE | 26 44 062 | 9/1976 |
| EP | 0 274 178 | 7/1988 |
| EP | 0 990 444 A2 | 4/2000 |
| FR | WO 97/43615 | 11/1997 |
| GB | 1 583 023 | 1/1981 |
| WO | WO 97/15228 | 5/1997 |

OTHER PUBLICATIONS

International Search Report dated Sep. 11, 2002.
Jonathan D. Sackner–Bernstein, MD et al., "How Should Diuretic–Refractory, Volume–Overloaded Heart Failure Patients Be Managed?" The Journal of Invasive Cardiology, vol. 15, No. 10 (Oct. 2003), pp. 585–590.
Brian E. Jaski, MD et al., "Peripherally Inserted Veno–Venous Ultrafiltration for Rapid Treatment of Volume Overloaded Patients", Journal of Cardiac Failure, vol. 9, No. 3, (Jun. 2003), pp. 227–231.
Lauer, A. et al, "Continuous Arteriovenous Hemofiltration in the Critically Ill Patient, Clinical Use and Operational Characteristics," Annals of Internal Medicine 99:455–460 (1983).

(Continued)

Primary Examiner—Angela D. Sykes
Assistant Examiner—Leslie R. Deak
(74) Attorney, Agent, or Firm—Nixon & Vanderhye, P.C.

(57) ABSTRACT

An integrated disposable cartridge for dialysis or ultrafiltration treatment of blood is disclosed that includes integral miniature pressure sensors. Sensors are embedded in the tubing of the cartridge to measure pressure of blood or other fluids. Cartridge elements form a continuous smooth bore passage for blood that reduces probability of clotting.

31 Claims, 7 Drawing Sheets

U.S. PATENT DOCUMENTS

| | | | | |
|---|---|---|---|---|
| 5,756,900 | A | * | 5/1998 | Arie et al. .................. 73/756 |
| 5,762,805 | A | | 6/1998 | Truitt et al. |
| 5,776,345 | A | | 7/1998 | Truitt et al. |
| 5,876,611 | A | | 3/1999 | Shettigar |
| 5,906,589 | A | | 5/1999 | Gordon et al. |
| 5,910,252 | A | | 6/1999 | Truitt et al. |
| 6,090,048 | A | | 7/2000 | Hertz et al. |
| 6,171,253 | B1 | * | 1/2001 | Bullister et al. ............ 600/486 |
| 6,272,930 | B1 | * | 8/2001 | Crozafon et al. .......... 73/729.2 |
| 2001/0016699 | A1 | | 8/2001 | Burbank et al. |
| 2001/0037079 | A1 | | 11/2001 | Burbank et al. |
| 2001/0041892 | A1 | | 11/2001 | Burbank et al. |
| 2002/0103453 | A1 | | 8/2002 | Burbank et al. |
| 2002/0147423 | A1 | | 10/2002 | Burbank et al. |

OTHER PUBLICATIONS

Verbanck, J. et al, "Pure Ultrafiltration by Repeated Puncture of a Peripheral Arm–Vein as Treatment of Refratory Edema", The International Journal of Artificial Organs, vol. 3, No. 6 (1980), pp 342–343.

Silverstein et al, "Treatment of Severe Fluid Overload by Ultrafiltration," The New England Journal of Medicine, vol. 291, No. 15, Oct. 10, 1974, pp. 747–751.

Blake, P. et al, "Refractory Congestive Heart Failure: Overview and Application of Extracorporeal Ultrafiltration," Critical Care Nephrology, *Advances in Renal Replacement Therapy*, vol. 3, No. 2 (Apr. 1966), pp. 166–173.

Civati G. et al, "Haemofiltration Without Substitution Fluid," Proc. EDTA–ERA, vol. 21 (1984), pp. 441–446.

Jenkins, R.D. et al, "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function By Dialysis, $4^{th}$ Ed., (1996) pp. 391–397.

Gupta, B.B. et al, "High Shear Rate Hemofiltration: Influence of Fiber Dimensions and Shear Rates," Artificial Organs, International Society for Artificial Organs, vol. 13(2) (1989), pp. 97–102.

Rimondini, A. et al, "Hemofiltration as Short–Term Treatment for Refractory Congestive Heart Failure," The American Journal of Medicine, vol. 83, Jul. 1987, pp 43–48.

Donato, L. et al, "Treatment of End–Stage Congestive Heart Failure by Extracorporeal Ultrafiltration," The American Journal of Cardiology, vol. 59, (Feb. 1, 1987), pp. 379 and 380.

L'Abbate, A. et al, "Ultrafiltration: A Rational Treatment for Heart Failure," Cardiology 1989; 76:384–390.

Chen, Y. et al, "Direct Peripheral Venopuncture: Another New Choice of Temporary Vascular Access", R nal Failure, 22(3), 369–377 (2000).

PRISMA® M60 Set, "Instructions for Use", pp. 1–6 and 12.

* cited by examiner

BLOOD PUMP HAVING A DISPOSABLE BLOOD PASSAGE CARTRIDGE WITH INTEGRATED PRESSURE SENSORS

FIELD OF THE INVENTION

This invention relates to an apparatus for the extracorporeal treatment of blood. More specifically, the invention relates an apparatus to treat patients by removing excessive fluids, such as water, from the blood of patients suffering from fluid overload.

BACKGROUND OF THE INVENTION

1. Mechanical Fluid Removal Therapies

Patients that exhibit symptoms of body fluid overload retain excessive amounts of fluid in the abdomen, legs and lungs. For example, excessive fluid in the lungs, referred to as edema, can cause patients to have difficulty breathing. Moreover, edema in the lungs leads to poor blood oxygenation. Poor oxygenation leads to acidosis and deleterious neurological and hormonal phenomena that increases vasoconstriction and load on the heart. In addition, vasoconstriction leads to reduced blood flow to the kidneys and diminishes the effectiveness of the main pharmacological means of fluid removal—diuretic treatment. The reduced blood flow can result in kidney failure.

Different modalities of Continuous Renal Replacement Therapy (CRRT) have been used to treat patients suffering from excess fluid overload and acute renal failure. In the acute condition, CRRT has been performed using standard methods of hemodialysis and continuous arterio-venous hemofiltration (CAVH). More recently, continuous veno-venous hemofiltration (CVVH) has been used to reduce the complications associated with such issues as hemodynamic instability and need for arterial access.

Hemodialysis and hemofiltration can be used to remove excess fluid from a patient, especially in patients whose kidneys have failed. The term "Renal Replacement Therapy" generally refers to all forms of dialysis, solute and fluid balancing therapy. Another category of patients affected by fluid overload are those with congestive heart failure (CHF). Patients suffering from CHF have weakened hearts that are unable to provide normal blood flow to the kidney and organs of the body. CHF patients may have normal kidneys, but lack sufficient blood flow to maintain proper kidney functions of removing excess fluid, e.g., water, from the body. The build-up of excessive fluids due to inadequate kidney functions further increases the blood pumping load on the heart, which is already suffering from CHF.

Renal replacement therapy performs two primary functions: ultrafiltration (removal of water from blood plasma), and solute clearance (removal of different molecular weight solid substances from blood plasma). The filter utilized, also called hemofilter or "dialyzer", can be set up to perform either or both of these functions simultaneously, with or without fluid replacement. Similarly, the various modes of renal replacement therapy relate to whether fluids, solutes or both are removed and whether fluids are replaced. "Clearance" describes the removal of substances, both normal and waste product, from the blood whether by kidney function or during renal replacement therapy.

Dialysis is the diffusive transfer of small solutes out of a blood plasma compartment by diffusion across the membrane itself. It occurs as a result of a concentration gradient, with diffusion occurring from the compartment with higher concentration (typically the blood compartment) to the compartment with lower concentration (typically the dialysate compartment). Since the concentration of solutes in the plasma decreases, clearance is obtained, but fluid may not be removed. Ultrafiltration can be combined with dialysis.

Hemofiltration is the combination of ultrafiltration and fluid replacement, typically in much larger volumes than needed for fluid control. The replacement fluid contains electrolytes, but not other small molecules. Since the net effect of replacing fluid without small solutes and ultrafiltration of fluid with small solutes results in net removal of small solutes, clearance is obtained.

Existing renal replacement therapy machines and specifically those used in acute setting to perform (Slow Continuous Ultrafiltration) SCUF and CVVH therapy were designed to primarily perform hemofiltration and hemodialysis, not merely fluid removal. Blood is composed of cellular components suspended in the fluid component called plasma. Water is the primary constituent of plasma in which physiological solutes such as sodium and potassium are dissolved. Also, in plasma, larger molecules, such as proteins and blood cells, are suspended. Hemofiltration and hemodialysis remove solutes (and some larger molecules) in addition to fluid removal. Ultrafiltration relates to fluid removal from blood, and does not remove solutes or larger molecules.

Ultrafiltration and hemofiltration operate primarily by convection. In hemofiltration, a solute molecule is swept through a filter membrane by a moving stream of ultrafiltrate. Proteins and blood cells are retained in the blood by the membrane. In patients with renal failure, renal replacement therapy, such as hemofiltration or dialysis, removes undesired solutes. In renal replacement therapy, vital elements such as electrolytes are also removed from the blood and need to be replaced to maintain electrolyte balance. Thus, hemofiltration and dialysis treatments usually require fluid replacement. In contrast, ultrafiltation does not remove substantial amounts of electrolytes and solutes.

During hemofiltration solute removal is entirely dependent on convective transport. Hemofiltration is relatively inefficient for solute removal, as compared to dialysis. Hemodialysis allows the removal of water and solutes by diffusion across a membrane in the direction of the concentration gradient. Diffusion transfers solute molecules across the membrane in the direction of the lower solute concentration at the rate inversely proportional to the molecular weight.

Hemodialysis requires a large filter membrane surface to enable effective solute clearance by diffusion. Hemofiltration requires large amount of ultrafiltrate to be transferred across the membrane to remove a relatively small amount of solute. This is a consequence of convection being an inefficient method of solute transport. Large amounts of fluid such as 1 to 4 liters per hour (L/hour) are continuously being removed during CVVH. The resulting loss of water and electrolytes are immediately dangerous to the patient. To maintain fluid and electrolyte balance, equally large or slightly lower amount of replacement fluid is infused into the patient. Replacement fluid is thus added into the extracorporeal blood circuit before or after the filter.

Ultrafiltration utilizes extracorporal blood filters to remove fluids from blood, where the filter generally includes a blood passage having input and output ports, a filtered fluid discharge port and a finely porous membrane separating the blood passage and the ultrafiltrate of filtrate discharge port. Ultrafiltration involves the convective transfer of excessive fluid out of the blood plasma from the blood passage, through pores in the membrane, and to the discharge port of the filter. The pores filter electrolytes and small and middle sized molecules (up to 20,000 to 30,000 daltons) from the blood plasma. Importantly, since the concentration of small solutes is the same in the ultrafiltrate as in the plasma, effectively, no clearance of solutes from the blood plasma occurs during ultrafiltration. Accordingly, the ultrafiltrate output from the filter is substantially all fluids, e.g., water, and is relatively free of solutes.

2. Limitations of Existing Devices for Ultrafiltration

Dialysis machines historically used sets of disposable components that are assembled of various parts from different manufacturers. This allowed flexibility but had certain disadvantages. Joints between component parts may leak, allow ingress of air and facilitate blood clotting. High skill was required from hospital nurses and technicians to assemble tubes, connectors, filters and accessories and then load them correctly into pumps, bubble detectors, pressure sensors and other interface elements of a dialysis machine. In the setting of a chronic dialysis center such practice was acceptable. However, in an acute setting, such as an Intensive Care Unit (ICU) of a hospital, the complexities of dialysis machines became an impediment.

As a result, use of mechanical fluid removal in the ICU, Emergency Rooms and general floors of a hospital has been limited. One United States manufacturer recently released sophisticated apparatus marketed under the tradename "Prisma"™ by Hospal-Gambro. It uses an integrated set of disposable dialysis components in which tubing, filter and accessories are bonded together and no assembly is required. The filter, sensor interfaces and four dedicated pump segments (for blood, dialysate, replacement solution and effluent) are mounted on a flat plastic cartridge to simplify the loading of the dialysis pumps. The Prisma™ machine is advertised as "an integrated system for continuous fluid management and automated renal replacement therapy blood."

While Prisma™ has been a significant advancement in the state of the art and has enjoyed wide adoption, it has its deficiencies. One deficiency is that, although the Prisma™ set of disposable dialysis components is continuous and bonded together, it does not present a smooth blood path but incorporates elements that create stagnant and slow moving blood zones. In such zones blood clots are likely to form. It also employs an interface to pressure sensors that is relatively inaccurate, unreliable and requires maintenance. There is a need for an improved design of the blood flow dialysis set that is simple to use, requires no maintenance or special training, and has improved performance over the existing set of disposable components for the Prisma™ machine.

In addition, the Prisma™ set does not integrate pressure sensors. Instead it integrates pressure "pods" shaped as domes. The interface surface of a pod is made out of silicon membrane approximately one inch in diameter. When mounted on the Prisma™ machine pods interface with the permanently installed pressure sensors that are the part of the machine. The interface is sealed by a rubber gasket so that the pod membrane serves as a lid on the pressure transducer cavity. When in operation, blood and other fluids flow through pods and come in contact with the membrane.

Pressure pods provide a means to measure the pressure of blood and other fluids flowing outside an interface surface. When the pressure inside the pod is increased the diaphragm stretches and thereby compresses the air inside a transducer cavity. As a result pressure in the bloodline or a fluid line is measured. The pod membrane serves as a barrier between the blood and potential contamination from environment, as is similar to the clinical invasive vascular blood pressure measurements. This method, although functional, has several deficiencies:

1. To be accurate pods have to be positioned perfectly when the pressure inside is atmospheric. Over time, if there is even a miniscule leak on the transducer side of the membrane, pod will creep and gradually stop transmitting pressure accurately because of the tension in the membrane.
2. Stretchable membranes and air filled transducer cavities add compliance to the circuit. Compliance is a delay in a pressure measurement due to the time required to stretch the pods and compress the air inside the pod cavity. Compliance is not desired since it makes the system less responsive to controls.
3. Pods filled with blood increase the blood-plastic contact surface and create stagnant zones with low blood flow velocity that facilitate clot formation. Because clots may form in the pods, the use of pods also necessitates the use of clot capture devices.
4. Pod domes have significant volume that increases the total extracorporeal volume of blood. This increased volume also increases the time that blood spends in contact with foreign materials. Altogether this increases risks of blood loss, hypotension and clotting.

SUMMARY OF THE INVENTION

To better address the needs of fluid removal and dialysis in the acute and emergency setting and to eliminate significant limitations of existing designs, applicants have developed a device that integrates all elements needed for successful blood treatment for ultrafiltration in one disposable set of components. This component set includes the tubing and filter that forms a blood path from the patient through the ultrafiltration machine and a return to the patient. The set also includes the pressure sensors apparatus for various types of blood treatments.

Extracorporeal blood treatments are known in the prior art where blood is continuously withdrawn from, processed and returned into the same or different vein in the patient's arm. For example, such methodology is commonly used in blood apheresis treatment. Examples of apparatus for plasma apheresis are marketed by Spectra™ or Trima™ from Gambro. However, extracorporeal blood treatment that draws blood solely from peripheral veins, e.g., the arms, has been limited. The major limitation of peripheral access is the relatively modest amount of blood that can be withdrawn per unit of time. It is accepted that in almost all patients the blood flow of 40–60 mL/min can be established. In some cases, blood flow of up to 100 mL/min can be achieved. Blood flow available from a peripheral vein is a great deal lower than the blood flow of 100–400 mL/min that is required to operate current renal replacement therapy machines, such as the Prisma™ system in an adult patient.

The apparently insufficient blood flow from a peripheral vein was perceived by the engineering and medical community as a prohibitive factor in using peripheral access for renal replacement therapy. In spite of an apparent clinical need, the peripheral vein ultrafiltration was never developed or actively investigated. Contrary to the conventional wisdom regarding the blood flow requirement, applicants analyzed the medical and engineering considerations behind the requirement for blood flow for renal replacement therapy.

They developed a clinically useful method and apparatus for fluid removal that can operate at blood flows of less than 100 ml/min and preferably of 40 to 60 ml/min.

The invention integrates the filter with the blood path tubing to and from the patient. The present invention has several distinguishing features that constitute an improvement over the state of the art. It incorporates an intravenous extracoraporal circuit that is disclosed in commonly owned (U.S. patent application Ser. No. 09/618,759, filed Jul. 18, 2000) and is hereby incorporated by reference. This extracorporal circuit provides blood flows of 10 to 60 ml/min, which is sufficient to remove excessive fluids from the blood via ultrafiltration. A straightforward dependency exists between the amount of ultrafiltrate removed from the blood and the flow (volume per unit time) of blood that passes through the filter. Blood condenses in the filter. In practice approximately 20% to 30% of the ultrafiltrate volume can be safely removed from the blood as filtrate. If more is removed, the blood becomes too dense with red blood cells and protein and will flow sluggishly. By removing 20% to 30% as ultrafiltrate, sufficient excess fluid may be removed by filtering just 2% or less of the total cardiac output of the patient. This 2% of cardiac output T can be removed through peripheral veins. Thus, an ultrafiltrate system has been a developed that requires only peripheral vein access.

The proposed invention integrates single use pressure sensors with the single use blood set. After being used on one patient, the entire set including the pressure sensors is discarded. Disposable pressure sensors are a part of the disposable blood circuit. The integrated sensors do not disturb the laminar blood flow inside the bloodline since the internal diameter of the sensor element is the same as of the blood tubing (3.2 mm or 4.5 mm). The sensing element is less than 5 mun in diameter and is embedded flush in the wall of the sensor housing. The housing is bonded flush with the internal wall of the blood line tube to form a continuous channel. Although similar disposable blood pressure sensors (such as ones made by Merit Medical of Utah) are used widely for invasive blood pressure measurement this design has never been previously used in an apparatus for fluid removal or as an integral part of a extracorporeal blood treatment set.

Pressure sensors are included as the integral elements of the blood circuit. The pressure sensor component includes a blood passageway coaxial to and integral with the passageway of the lumen of the blood circuit. For example common blood tubing internal diameters of 3.2 and 4.5 mm can be used for the blood passageway in the pressure sensor. A small silicone or other flexible material filled window in the wall of the tubing separates blood from the pressure sensitive element. This way there is no disturbance to the smooth flow of blood to facilitate clotting. There is no stagnant zone where blood is not moving. There is no added compliance since there is virtually no compressible gas in the system and the silicone filled window can be made as small as 1 to 5 mm$^2$. In addition, if the sensing element of the sensor is compatible with blood there is no loss of accuracy associated with the transmission of pressure through the diaphragm. The frequency response of the sensor is also vastly improved since there is no significant compliance in the measuring element.

SUMMARY OF THE DRAWINGS

A preferred embodiment and best mode of the invention is illustrated in the attached drawings that are described as follows.

DETAILED DESCRIPTION OF THE INVENTION

Figure 1:
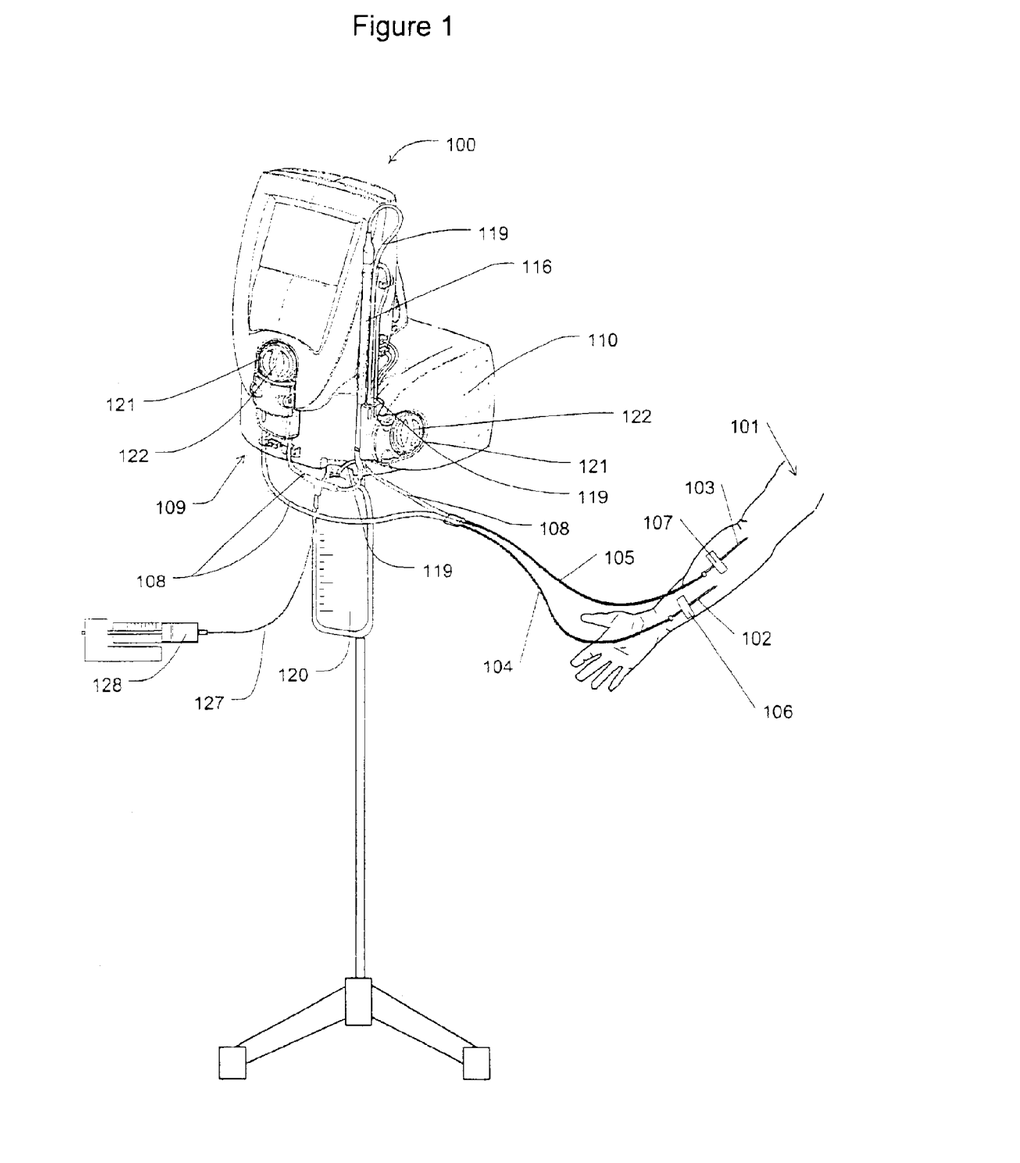
FIG. 1 is a perspective view of a intravenous blood ultrafiltration system having a first embodiment of a disposable blood circuit cartridge with an integrated pressure sensor.

FIG. 1 shows an intravenous blood ultrafiltration system 100 for treating a patient suffering from fluid overload. The patient 101, e.g., a human or other mammal, can undergo ultrafiltration treatment to remove fluid, e.g., water, from his blood while lying in bed or sitting in a chair. The patient can be in a physician's office, outpatient clinic, hospital emergency room or other medical treatment center. The center need not be an ICU or other intensive treatment unit.

To initiate ultrafiltration treatment, two standard 18G IV needles 102 and 103 are introduced into suitable peripheral veins (on the same or different arms) for the withdrawal and return of the blood. The needles are attached to withdrawal tubing 104 and return tubing 105, and secured to skin with attachments, such as adhesive strips 106 and 107. The withdrawal and return tubing form portions of a continuous blood fluid passage 108 that extends through a disposable blood circuit cartridge 109.

Figure 7:
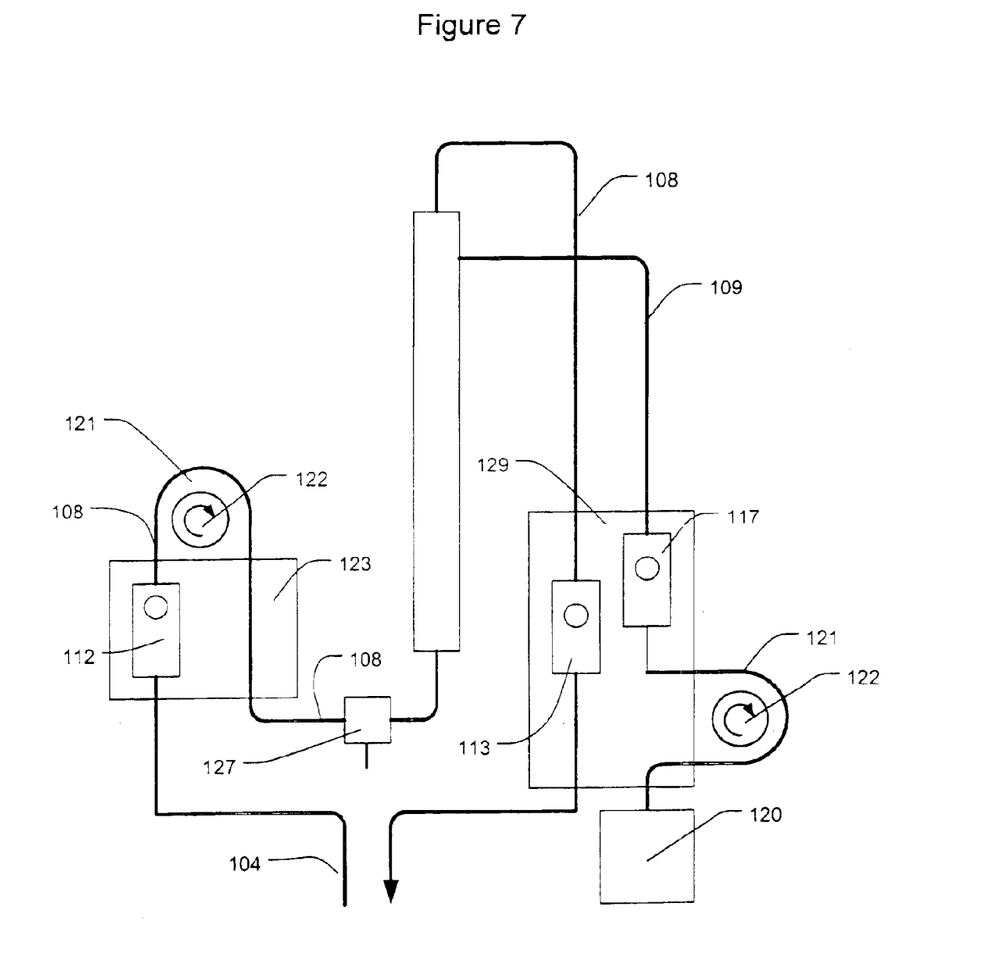
FIG. 7 is a schematic diagram showing a fluid path of blood and removed fluids for the blood cartridge.

The disposable blood circuit cartridge 109 is attached to a pumping console 110. The cartridge may be detached from the console, as is shown in FIG. 7. The cartridge 109 includes the continuous blood passage 108 through which flows blood withdrawn from the patient. After flowing the cartridge, the blood is returned to the patient via return tubing 105.

The blood passage 108 through the cartridge 109 supports a continual flow of blood, and is substantially free of stagnation areas in which blood might pool and coagulate. In addition, the blood passage is generally free of air interfaces so that the blood while in the cartridge does not encounter blood-air interfaces. If the blood were permitted to be exposed to air, the blood would begin to coagulate and the coagulated blood could form occlusions in the passage or flow back into the blood vessel of the patient.

The blood passage 108 includes the blood tubing 104 leading from and blood tubing 105 leading to the patient for withdrawing and reintroducing blood into the patient. Similar tubing sections extend through the cartridge and form additional links in the passage 108. These tubing links are coupled to a blood filter 111 and pressure sensors 112, 113, that are contiguous with the tubing and form sections of the blood passage 108. All sections of the blood passage, including the filter and sensors, are continues flow sections, such as formed by a hollow tube with smooth cylindrical sides. The pressure sensors have hollow straight-tube blood passages with a small pressure sensor mounted flush with the wall of the sensor tube so as to avoid obstructing the blood flow. Similarly, the filter has continuous blood flow passages that avoid areas of stagnate blood.

Figure 10:
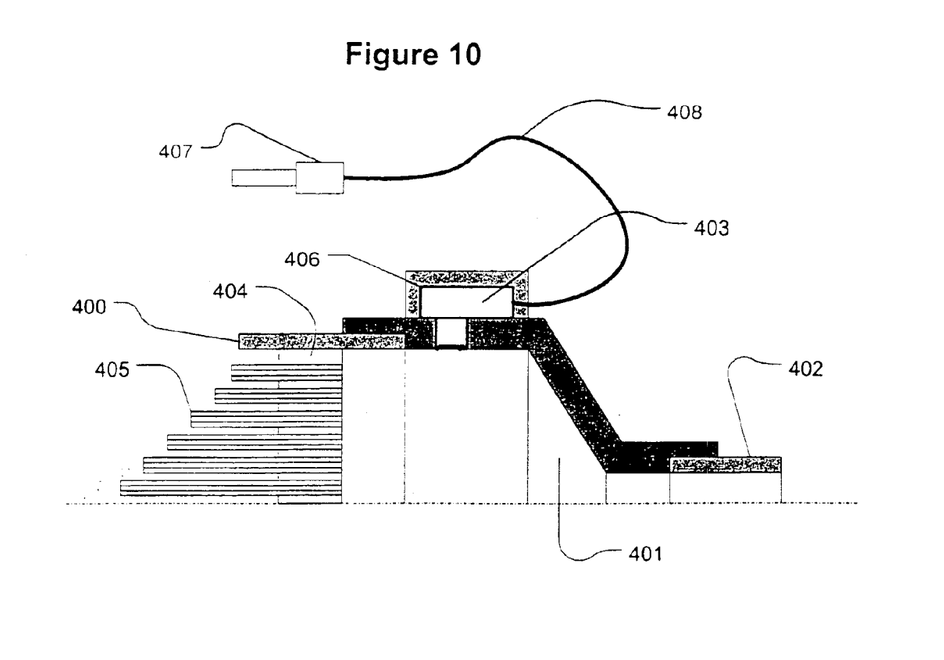
FIG. 10 is partial cross-sectional view of an integral disposable pressure sensor in a filter section of a blood circuit cartridge.

The blood filter 111 may be a cylindrical tube 400 having a conical blood inlet 401 and a conical blood outlet, each coupled to the tubing of the blood passage 108, as is shown in FIG. 10. The hollow tube 400 of the filter 111 includes an open cylindrical filter entrance 401 having a pressure sensor 403 mounted on the wall of the inlet. A pressure sensor on the filter is optional and is now shown in FIG. 1. The filter is packed with porous hollow fibers 405 arranged in parallel with each other and the axis of the filter. These fibers 405 are each open to blood flow at the inlet 401 of the filter and discharge blood at their outlets in an outlet section of the filter. The filter fibers have cylindrical walls that are formed of a porous membrane. Blood cells and proteins does not pass through the walls of the filter fibers, but filtrate solution, e.g., water, ions and small molecules, does pass through the porous fiber walls. The membrane in the walls of the filter fibers 405 separates the blood flowing through the fiber into a blood component (which flows through the fiber, via the outlet section of the filter and the blood return tubing, and back into the patient) and a filtrate component (which is discharged through filtrate line 119 into the ultrafiltrate bag 120). The filtrate disposable blood circuit cartridge 109 is supplied separate from the console and packaged in a sterile package (not shown). See FIG. 8. The cartridge is intended to be used for one single treatment, and not to be reused. The cartridge is inserted into the pump console 110 by threading the tubing loops 121 in the blood passage 108, and ultrafiltrate discharge tubing 119 over the rims of roller pumps 121 and 122. As the pumps rotate, they slidably engage the tubing and force blood and ultrafiltrate fluids to move through the cartridge fluid passages. The microprocessor pump drivers control the flow rate of the blood and ultrafiltrate through the cartridge. The pump drivers are part of the console and are controlled by a computer system within the console. However, the console and its pumps are not part of the present invention. The present invention is embodied in the disposable blood circuit cartridge. Once the cartridge is installed to the console (as shown in FIG. 1), the system is primed with a sterile priming solution. The needles for the withdrawal tube 104 and the return 105 tube are inserted into a peripheral blood vessel(s) of the patient 101. Tubes can be connected to the needles and blood displaces the priming solution. Treatment can begin as common in fluid removal or dialysis.

Figure 2:
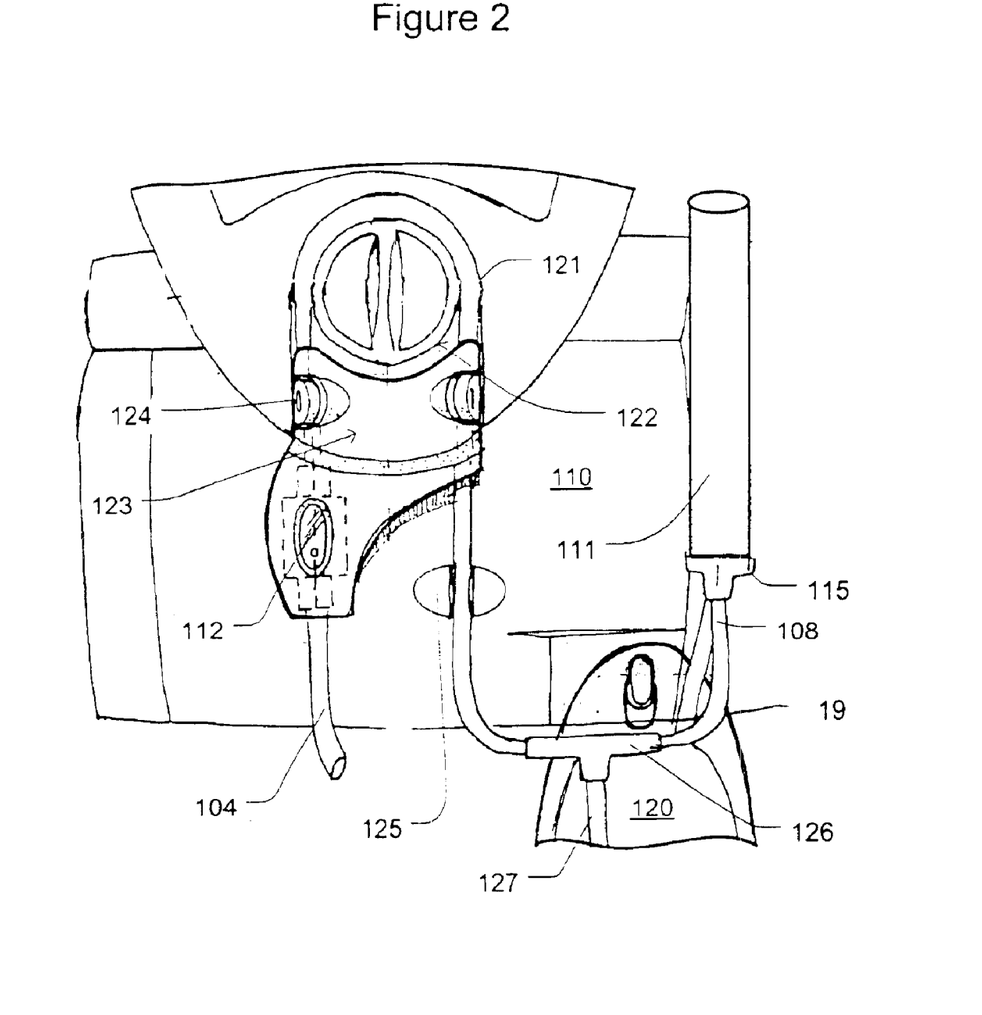
FIG. 2 is a font view of a first portion of the blood circuit cartridge.
Figure 3:
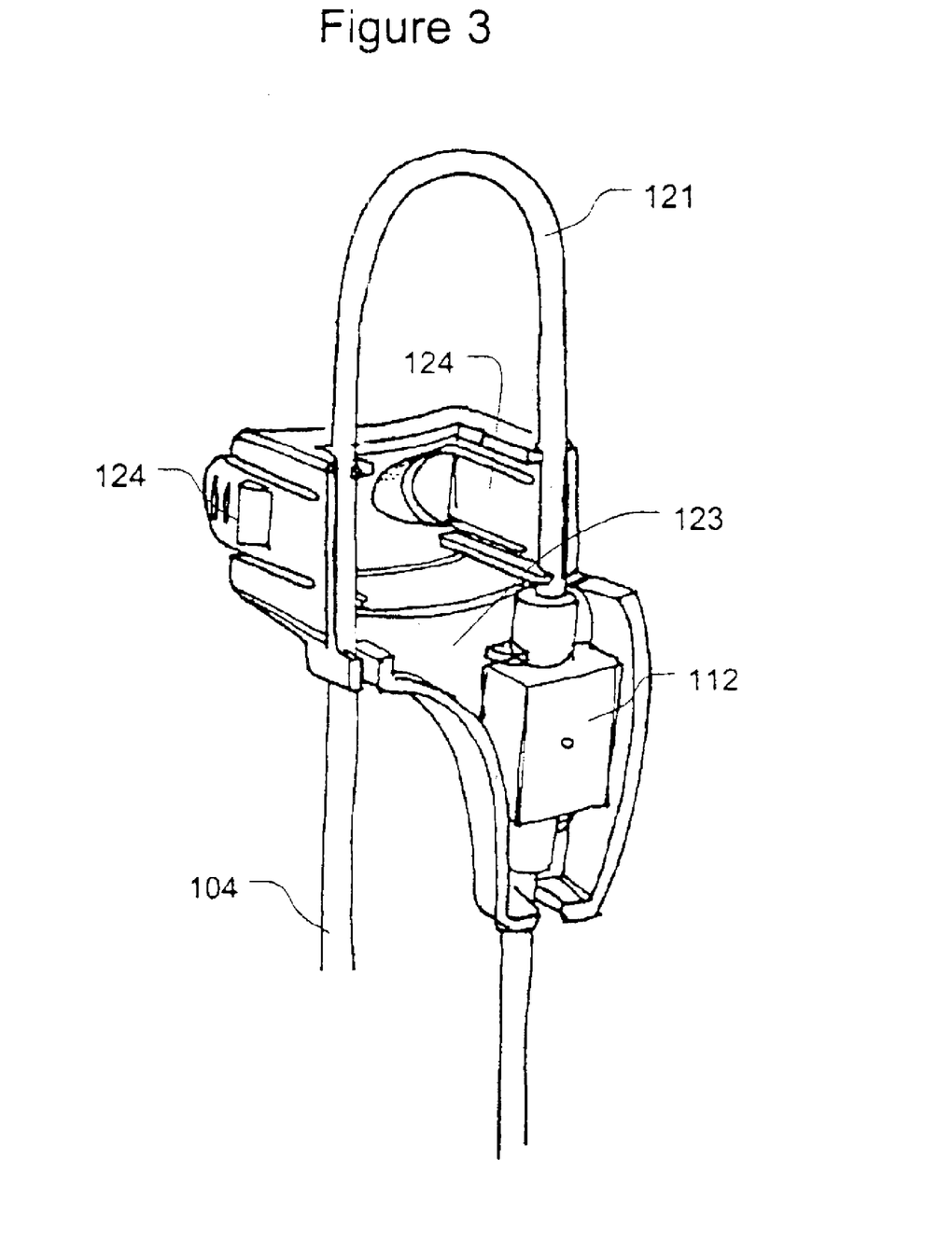
FIG. 3 is a rear view of the first portion of the blood circuit cartridge shown in FIG. 2.

FIG. 2 is a close-up front view of a portion of the cartridge 108 fitted on the pump 122. FIG. 3 is a close-up rear view of the same portion of the cartridge, but removed from the console. The tubing of the cartridge may be mounted in a molded-plastic housing 123 that fits into a recess in the surface of the console and snaps into the console with latches 124. A blood withdrawal pressure sensor 112 is mounted to an inside surface of the cartridge housing 123. The console may include clips 125 to hold the tubing in place, in addition to the recess and latch coupling between console and the cartridge housing 123. The clips 125 on the housing may incorporate a bubble detector to sense bubbles flowing in the blood passage of the cartridge.

The blood passage 108 may include a T-connector 126 so that medicines and drugs can be introduced into the blood flowing through the passage. These medicines and drugs would flow through a tube line 127 from an injection pump 128 to the connector 126 and into the blood passage.

Figure 4:
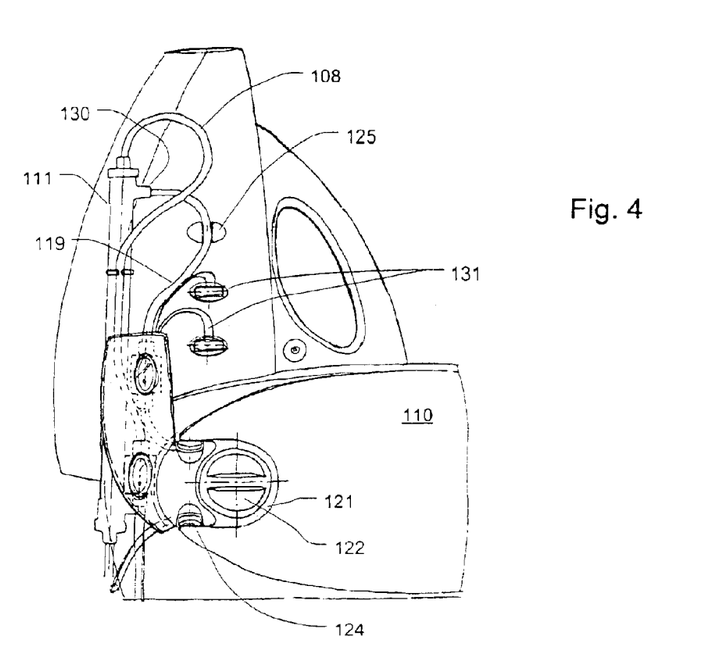
FIG. 4 is a side view of a second portion of the blood circuit cartridge.
Figure 5:
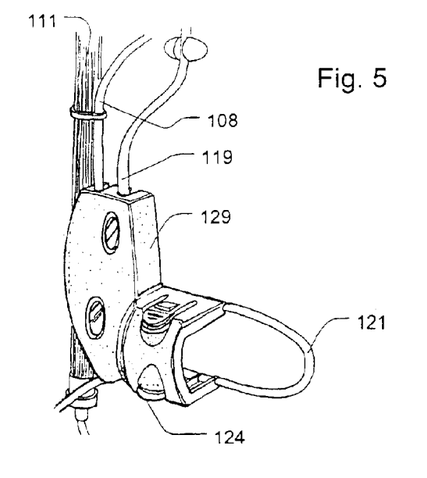
FIG. 5 is a perspective view of the second portion of the blood circuit cartridge.
Figure 6:
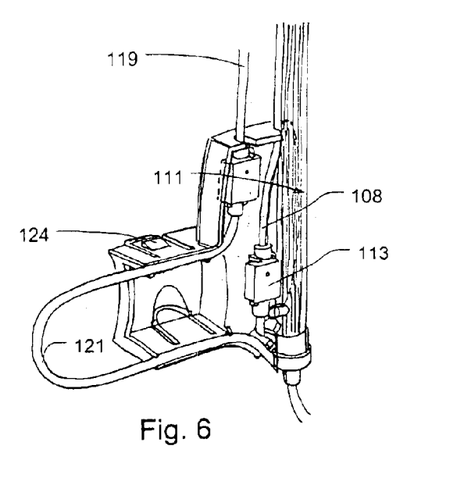
FIG. 6 is a rear view of the second portion of the blood circuit.

FIGS. 4 to 6 show a second cartridge housing 129 for supporting the filter 111 and the tubing loop 121 that is threaded into the rim "raceway" of the pump 122 that moves filtrate from the filtrate output 130 of the filter through the filtrate line 119 to the bag 120. The filter may snap into or be bonded to the second cartridge housing. The filter is mounted vertically in the console. The blood inlet is at the lower end of the filter and the outlets for the blood and filtrate are at the top. The pressure sensor 132 for the filtrate tube, and a sensor 113 for the blood return tube 105 are mounted to an inside surface of the second cartridge housing 129. The pressure sensors 112, 113 and 117 may include transducers that convert pressures into electrical signals carried by signal wires 131 that are connected to a computer controller in the console.

During operation, the ultrafiltration system 100 (including pump console and disposable blood circuit cartridge) requires minimal intervention from user. User sets the maximum rate at which fluid is to be removed from the patient using a control panel on the console. Blood circulates through the blood passage in the cartridge. As the blood passes through the filter 111, ultrafiltrate is removed from the blood and is discharged from the filter into the ultrafiltrate tubing 119 and is collected into a graduated collection bag 120. When the bag is full (as detected by a bag weight sensor in the console), the console issues an alarm and ultrafiltration stops until the bag is emptied.

FIG. 7 is a schematic diagram of the blood and filtrate flow through the ultrafiltration system 100. Blood is withdrawn from the patient through an 18 Gage withdrawal needle 102, flows into the withdrawal tubing 104 and enters the blood passage 108 of the cartridge 123. The needle is inserted into a suitable peripheral vein in the patient's arm or any other suitable peripheral vein. Blood flow through the withdrawal tubing is controlled by the speed of the roller pumps 122. Before entering the pump, blood passes through approximately two meters of plastic withdrawal tubing 104. This tubing may be formed of medical PVC of the kind used for IV lines and has internal diameter (ID) of 3 mm. The tubing for the pump loop 121 has the same ID as do other portions the tubing in the blood passage. During operation, the pump rollers compress the pump segment tubing. The rotational speed (RPM) of the pump governs the fluid flow rate through the tubing. The pump may rotated by a DC motor in the console, and is under microprocessor control. The system may pump approximately 1 ml (milliliter) of blood for each full rotation of the pump 122 and, for example, a pump speed of 60 RPM provides a flow rate of 60 ml/m (milliliters/minute).

Pressure sensors 112, 113 are integral to the blood passage 108 in the cartridges 123 and 129. These sensors are disposed in the passage 108 such that a diaphragm of the sensor, which is the device that is in fluid contact with the load and directly responds to the blood pressure, is adjacent the blood passage. The diaphragm does not form stagnant areas in the passage. Similarly, a pressure sensor 117 (which also includes a diaphragm in fluid contact with the filtered fluid) for the ultrafiltrate is integrally formed in the filtrate tubing 119 between the filter 111 and the ultrafiltration bag 120. These pressure sensors are included in the disposable cartridge and are intended for one-time use. The pressure sensors each have a generally straight and hollow fluid passage that is coupled to the blood or filtrate tubing in the cartridge. The passages in the sensors are contiguous with the blood and ultrafiltrate passages of the cartridge.

The fluid flow passage in each sensor includes in a peripheral wall a pressure sensing diaphragm that is relatively small compared to the passage. As blood or ultrafiltrate flows across the diaphragm, the pressure of the flow displaces the diaphragm. This diaphragm displacement is converted by a mechanical-to-electrical transducer in the sensor to an electrical signal, e.g., a voltage level, that is indicative of the pressure of the flow. The electrical signal is output by the sensor to the pump console 110 through an electrical signal line, e.g. a wire 131. A controller in the console receives the pressure signals via the lines 131 and determines the pressure level of the blood or ultrafiltrate in the blood or ultrafiltrate passage in which the associated sensor is positioned.

The advantages of the pressure sensors 111, 112 and 117 include that the fluid passage within the sensor is a smooth hollow tube through which the blood or ultrafiltrate flows without obstruction or stagnation; the sensors do not introduce a blood-air interface to the blood flowing through the cartridge, and they provide a direct electrical signal output that reliably indicates the pressure in the sensor passage. These pressure sensors are an improvement over existing blood flow pressure sensors that have bubble traps or separation diaphragms, which are less accurate, and have areas of stagnant blood flow.

The pressure sensors 111, 112 and 117 may be sufficiently sensitive to measure negative (suction) pressure to minus 400 mmHg (millimeter of mercury). The withdrawal pressure signal is used by the console to maintain the blood flow from the vein and through the withdrawal tube 104. Typically, a peripheral vein can continuously supply 60–100 ml/min of blood. The sensor can be applied to confirm that an acceptable flow of blood is being withdrawn from the vein by sensing pressure in the withdrawal tube, by adjusting the pressure reading for any height difference between the sensor 111 and the peripheral vein, and by compensating for flow resistance in the tubing 104 from the vein to the sensor.

If the pressure reading indicates that the blood flow has dropped significantly from the withdrawal vein, then the console may determine that the vein has an occlusion (such as a vein collapse) and reduce the speed of the pump or stop it altogether accordingly. For example, blood flow can be temporarily impeded by the collapse of the vein caused by patient movement, a crimp or kink in the tubing, or occlusion by clotting. In other cases the vein of the patient may not be sufficient to supply the maximum desired flow of 60 ml/min. Such conditions obstruct the blood flow and are detected by the blood withdrawal pressure sensor. The software executed by the microprocessor of the pump console controls the pump speeds such that the rate of flow in the blood passage of the cartridge 109 slows the withdrawal of blood to prevent or recover from the collapse of the vein and reestablish the blood flow based on the signal from the withdrawal pressure sensor. Similarly, a pressure signal from the sensor 112 may also be used to detect a disconnection in the withdrawal bloodline 104 from the needle 103. This condition is detected by the abrupt decrease of the withdrawal pressure generated by the pump. An occlusion in the withdrawal tube 104 may be caused by the collapse of a vein or a kink in the tube, and can result in a rapid decrease (more negative) of the pump suction pressure that is detected by the sensor 112 which signals a controller in the pump console. In response to this rapid pressure decrease, the controller may reduce the pump speed to slow the blood flow being withdrawn, or stop the pump and issue an alarm.

In addition, a pressure sensor 113 may be incorporated into blood passage of the cartridge 129 that is downstream of the pump 122 and filter 111. This return sensor 113 detects the pressure of the blood being returned to a peripheral blood vessel of the patient, and provides a signal indicative of the pressure of the flow of the return blood. The sensor signal is processed by a controller in the console, and may be used to detect abnormal conditions in the return tubing 105, such as an occlusion, an unacceptable clotting of the filter or a disconnection of the blood tubing with the pump, the filter 110, the return line or the catheter needle in the patient. In addition, the blood return circuit pressure sensor 113 and the signal from the filtrate pressure sensor 117 may serve also to determine a rate of filtrate flow into the bag 120. The ultrafiltrate sensor 117 may also to detect clotting or fouling of the filter 110 or the filtrate line 119.

Figure 8:
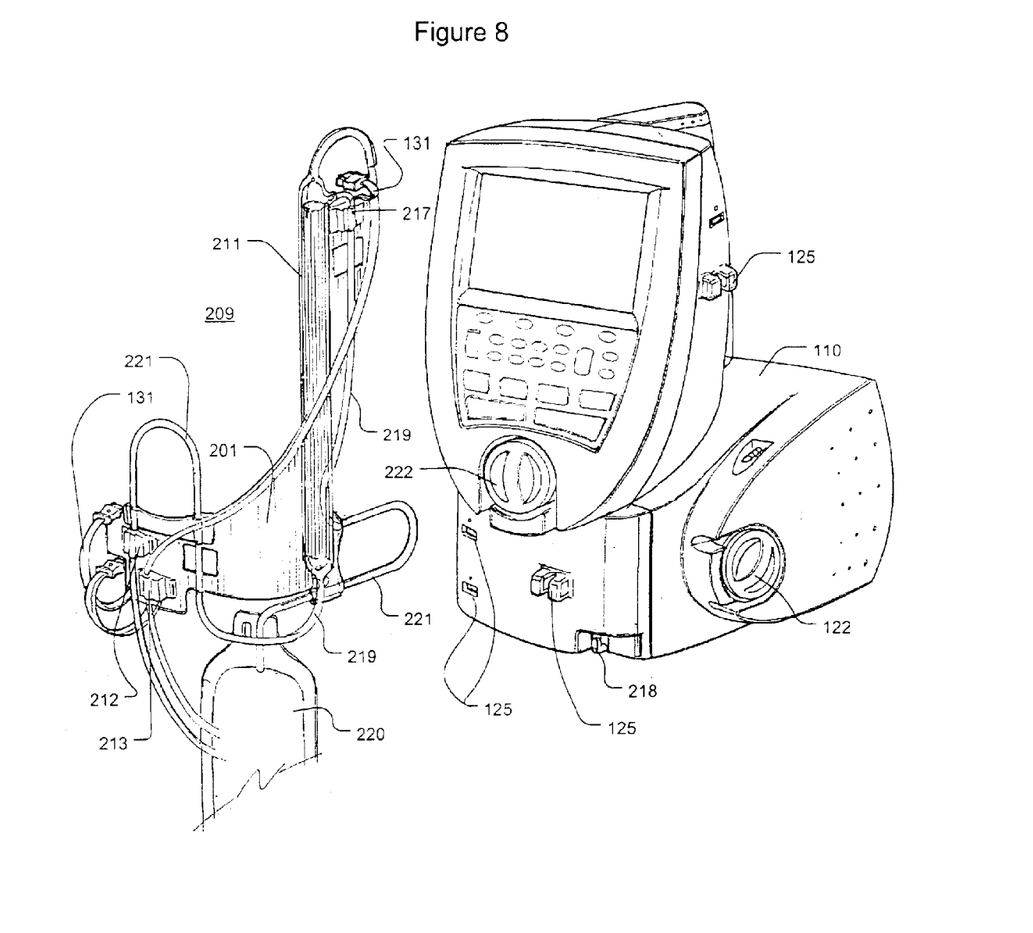
FIG. 8 is a view of a second embodiment of a disposable blood circuit cartridge, where the cartridge is shown separately from an associated pump console.

FIG. 8 shows an alternative embodiment of a disposable blood circuit cartridge 209. This cartridge is similar in many respects to the first blood circuit cartridge 109, but includes a substrate sheet 201 on which the blood passage 208, filter 211, pressure sensors 212, 213 and 217, and filtrate tube 219 are mounted. In addition, the cartridge 209 may include a filtrate bag 220 that is hung on a hook 218 on the console. This hook may be connected to a strain gage or pressure transducer to sense the weight of the bag and thereby provide a signal indicative of when the bag is full to a controller in the console. The substrate sheet is a molded plastic material formed to fit onto the console and align the loops 221 of the blood and filtrate passages with the roller pumps 122. In addition, attachment clips (not shown) on an inside surface of the substrate may connect to clip-holders 222 on the console. Blood passage tubes 208 and filtrate tube 219 are positioned by the attachments to the substrate 201 to facilitate loading into slots of the air detector 125 and the blood leak detector 125.

Figure 9:
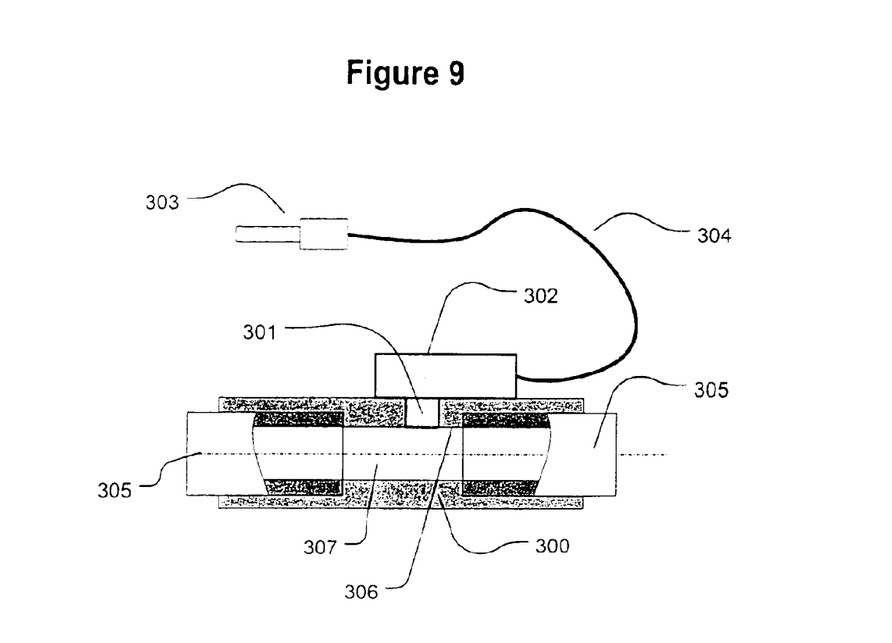
FIG. 9 is a partial cross-sectional view of an integral disposable pressure sensor in a tube section of a blood circuit cartridge.

FIG. 9 is a cross section drawing of a pressure sensor 300. The sensor includes a diaphragm 301 mounted flush with the inside surface of the wall 306 of the hollow tubular flow passage 307 in the sensor. The flow passage has a similar ID (Typically 3 or 4.5 mm) to that of the blood passage 305 which is coupled to is the inlet and outlet of the sensor. Accordingly, the flow passage 307 forms a contiguous section of the blood passage 305 with the tubing in the cartridge. The diaphragm 301 is deflected by the pressure of the blood flow through the passage 307. This deflection is sensed by a pressure transducer 302, e.g., a piezoelectric semiconductor, which generates an electrical signal indicative of the blood/filtrate pressure on the diaphragm. A signal wire 304 and a connector 303 transmits the sensor electrical signal to the controller in the pump console.

The sensors may be a flow-through type pressure sensor commonly used for blood pressure measurement. The sensor has a passage that is contiguous with the tubing for the blood passage or the ultrafiltrate tubing. The mechanical-to-electrical transducer of the sensor may be a strain gauge or capacitive circuit having a piezoresistive element implanted on an etched silicon diaphragm. The diaphragm is positioned at the periphery of the passage and flush with the wall of the passage so that blood or ultrafiltrate flows across the diaphragm without disturbing the flow. The pressure of the blood or ultrafiltrate acts on the diaphragm. The piezoresistive transducer element of the sensor is responsive to the stress induced on the diaphragm by an external pressure, such as the flow of blood or ultrafiltrate. A piezoresistive transducer can provide linear output in the form of an analog voltage that is proportional to pressure input and ratiometric with a supply voltage. High sensitivity, frequency response and excellent long-term repeatability make these pressure sensors suitable for the blood cartridge application.

The pressure sensor housing incorporates a monolithic silicon piezoresistor, which generates a changing output voltage with variations in applied pressure. The resistive element, which constitutes a strain gauge, is ion implanted on a thin silicon diaphragm. Applying pressure to the diaphragm results in a resistance change in the strain gauge, which in turn causes a change in the output voltage directly proportional to the applied pressure. Applying a voltage supply across the piezoresistor transducer element will force an electric current to flow through the element. Pressure applied to the piezoresistor via the diaphragm produces a change in the element resistance and a corresponding change in the output voltage of the sensor. This output voltage can be converted by the pump console into a corresponding pressure of the fluid, e.g., blood or ultrafiltrate, applied to the pressure sensor. Small inexpensive pressure sensors that are suitable for blood pressure measurements are sold by Motorola under the tradename Digital DNA™ (Digital Blood Pressure Meter, AN 1571/D).

FIG. 10 illustrates a cross-sectional view of a pressure sensor embedded in the wall of a filter housing 400 of a hemofilter, dialyzer or hemoconcentrator. These filters have hollow fibers 405 coaxial with the device tubular body 400. Filter fibers are embedded in the packing or potting material 404 in the cylinder of the filter. Blood tubing 402 is bonded or connected with a quick connector the filter header cap 401. A disposable pressure sensor 403 is assembled with the cap 401 with the pressure sensitive element 408 protruding through the wall and in contact with blood. The pressure sensor 403 is covered by a housing cover 406, and has electric wires 408 attached to the electric plug in connector 407. A similar sensor can be attached or embedded in the wall of the filter housing 400 to measure ultrafiltrate pressure in the space formed by the outer wall of the fibers 405 packing material 404 and the inner wall of the housing 400.

What is claimed is:

1. A disposable cartridge for mounting an extracorporeal blood passage on a pump device comprising:
   a. a first cartridge housing supporting said blood passage, wherein said first cartridge housing is configured to seat in a first recess of the pump device, wherein said blood passage has a blood inlet connectable to a vascular system of a patient and a blood outlet connectable to the vascular system such that blood flows through the blood passage;
   b. a blood pump coupling loop of the blood passage attached to the first cartridge housing and extending outwardly from said housing, wherein a blood pump of the device engages the pump coupling loop when said first cartridge housing is seated on the blood pump device;
   c. a second cartridge housing supporting said blood passage and a filtrate passage, wherein said second cartridge housing is distinct and separate from said first cartridge housing, wherein said second cartridge housing is configured to seat in a second recess of the blood pump device, and
   d. a filtrate pump coupling loop of the filtrate passage extending outwardly from said second cartridge housing, wherein a filtrate pump of the device engages the filtrate pump coupling loop when said cartridge housing is seat on the pump device, wherein through said filtrate passage flows filtrate withdraw from blood in the blood passage.

2. A cartridge as in claim 1 wherein said blood passage connects said first cartridge housing to said second cartridge housing.

3. A cartridge as in claim 1 wherein an electronic pressure sensor is fixed to the first cartridge housing and is arranged to sense a pressure of the blood flow through the blood passage, wherein said sensor outputs an electrical signal indicative of the blood flow pressure to the device.

4. A cartridge as in claim 3 where a second pressure sensor is to fixed to the second cartridge housing and said second pressure sensor is arranged to sense a pressure of filtrate flow through the filtrate passage, wherein said sensor outputs an electrical signal indicative of the filtrate flow pressure to the device.

5. A cartridge as in claim 4 where the second pressure sensor is embedded in the filter and is in fluid contact with the filtered fluid.

6. A cartridge as in claim 4 further comprising a third pressure sensor arranged to sense a blood pressure in return blood passage included with the disposable cartridge.

7. A cartridge as in claim 3, where the pressure sensor and the pump coupling loop of the blood passage are rigidly fixed to an underside of the first cartridge housing and the first cartridge housing detachably attaches to the pump device adjacent to a raceway of the blood pump and said raceway receives the loop.

8. A cartridge as in claim 7 where the blood passage is formed of transparent material so that the blood flow is visible.

9. A cartridge as in claim 7 wherein the cartridge is discarded after treatment of the patient and after being released from the pump device.

10. A cartridge in claim 3 where the pressure sensor is in fluid contact with the blood.

11. A cartridge as claim 3 wherein the pressure sensor is sealed in a pressure sensor housing formed of a biocompatible and flexible material, and the sensor housing includes an integral and flexible membrane in contact with the blood and electronic sensors.

12. A cartridge as in claim 3 wherein the pressure sensor includes a pressure responsive diaphragm exposed to the blood flow and a mechanical-to-electric transducer coupled to the diaphragm and having an electrical signal output indicative of the pressure of the blood.

13. A cartridge as in claim 12 wherein the mechanical-to-electric transducer includes a strain gain bridge or capacitive element to convert displacement of the diaphragm to said electrical signal.

14. A cartridge as in claim 3 further comprising electrical signal connectors extending from the pressure sensor on the cartridge to a detachable electrical coupling on the blood pump device.

15. A cartridge as in claim 1 wherein the filtrate passage extending from the second cartridge housing discharges filtrate fluid to a filtrate collection container.

16. A cartridge as in claim 1 further comprising a pressure sensor housing affixed to the first cartridge housing for the pressure sensor, where the pressure sensor housing includes a smooth tubular channel contiguous with the blood passage fixed to the first cartridge housing and the pressure sensor is mounted flush with a wall of the first cartridge housing.

17. A cartridge as in claim 1 wherein blood pump coupling loop of said first cartridge housing extends substantially vertical when attached to the pump device and the filtrate pump coupling loop of the second cartridge housing extends substantially vertical when attached to the filtrate pump.

18. A cartridge as in claim 1 wherein said first cartridge housing has an inside side surface facing the device when the first cartridge housing is seated on the device, and wherein said blood passage is attached to the inside surface of the first cartridge housing.

19. A cartridge as in claim 1 wherein said second cartridge housing has an inside side surface facing the device when the second cartridge housing is seated on the device, and wherein said filtrate passage and a filter are attached to the inside surface of the second cartridge housing.

20. A blood circuit as in claim 1 wherein said first cartridge housing is seated on a front of the device and the second cartridge housing is seated on a side of the device.

21. A blood circuit as in claim 1 further comprising a blood filter having an input and a blood output coupled to the blood passage and a filtrate outlet coupled to the filtrate line, wherein said filter is fixed to the second cartridge housing.

22. A cartridge as in claim 21 wherein the filter is of a group consisting of a hemodialyzer, hemofilter or hemoconcentrator, and the filter includes an integral pressure sensor embedded in a blood passage wall of the filter.

23. A cartridge as in claim 21 wherein the blood filter in the second cartridge housing is substantially vertical when said second cartridge housing is mounted in the device, and wherein said filter has a bottom filtered blood outlet to the blood passage.

24. A blood circuit as in claim 21 wherein said filter is oriented vertically on the second cartridge housing when said housing is mounted on the device, and said filter inlet is at a top of the filter.

25. A disposable extracorporeal blood circuit for processing blood from a mammal and attachable to a blood treatment device having a blood pump and a filtrate pump, said blood circuit comprising:

a blood passage having a blood withdrawal port connectable to a vascular system of the mammal, a blood return port connectable to the vascular system, and a blood passage between the withdrawal port and the return port through which blood flows wherein the blood passage has a smooth and continuous wall throughout the passage;

a blood filter having a blood inlet and a blood outlet coupled to said blood passage such that the blood flows through said filter, and said filter further comprising a filtrate output coupled to a filtrate line, a first cartridge housing to which is attached a blood loop of the blood passage and the pressure sensor, wherein the blood passage is mounted to an inside surface of the first cartridge housing such that the blood loop extends outwardly of the cartridge housing, and said first cartridge housing is detachably mountable to the blood treatment device to engage the blood loop to the blood pump when the first cartridge housing is mounted on the device, and a second cartridge housing to which is attached a filtrate loop of the filtrate line, wherein the filtrate line is mounted to an inside surface of the second cartridge housing such that said filtrate loop extends outwardly of the second cartridge housing, said second cartridge housing is distinct and separate from the first cartridge housing, and said second cartridge housing is detachably mountable to the device to engage the filtrate loop to the filtrate pump of the blood treatment device.

26. A disposable extracorporeal blood circuit as in claim 25 further comprising a pressure sensor fixed to the inside surface of the first cartridge housing and connected to the blood passage, wherein said pressure sensor outputs a signal indicative of a blood pressure in the blood passage.

27. A disposable extracorporeal blood circuit as in claim 25 wherein the tubular blood circuit line is connectable to a roller blood pump of the blood pump.

28. A disposable extracorporeal blood circuit as in claim 25 wherein the withdrawal and return blood vessels are the same blood vessel.

29. A disposable extracorporeal blood circuit as in claim 25 wherein the blood filter in the second cartridge housing is substantially vertical when said second cartridge housing is mounted in the device, and wherein said filter has a bottom filtered blood outlet to the blood passage.

30. A disposable extracorporeal blood circuit as in claim 25 wherein blood pump coupling loop of said first cartridge housing extends substantially vertical when attached to the pump device and the filtrate pump coupling loop of the second cartridge housing extends substantially vertical when attached to the filtrate pump.

31. A blood circuit as in claim 25 wherein said first cartridge housing is seated on a front of the device and the second cartridge housing is seated on a side of the device.

* * * * *